United States Patent
Yates et al.

(10) Patent No.: US 10,111,719 B2
(45) Date of Patent: Oct. 30, 2018

(54) CONTROL OF THE RATE OF ACTUATION OF TOOL MECHANISM BASED ON INHERENT PARAMETERS

(71) Applicant: Ethicon Endo-Surgery, LLC, Guaynabo, PR (US)

(72) Inventors: David C. Yates, West Chester, OH (US); Frederick E. Shelton, IV, Hillsboro, OH (US); Michael J. Vendely, Lebanon, OH (US); Jason L. Harris, Lebanon, OH (US); Mark D. Overmyer, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 52 days.

(21) Appl. No.: 15/237,704

(22) Filed: Aug. 16, 2016

(65) Prior Publication Data
US 2018/0049818 A1 Feb. 22, 2018

(51) Int. Cl.
*A61B 34/30* (2016.01)
*A61B 34/37* (2016.01)
(Continued)

(52) U.S. Cl.
CPC .............. *A61B 34/30* (2016.02); *A61B 34/37* (2016.02); *A61B 34/74* (2016.02); *B25J 9/04* (2013.01);
(Continued)

(58) Field of Classification Search
CPC ......... A61B 34/30; A61B 34/37; A61B 34/74; A61B 2034/742; A61B 2034/741;
(Continued)

(56) References Cited

U.S. PATENT DOCUMENTS 8,114,345 B2 2/2012 Dlugos, Jr. et al.
8,876,857 B2 * 11/2014 Burbank .......... A61B 17/07207
606/205

(Continued)

FOREIGN PATENT DOCUMENTS

EP  2526877 A1  11/2012

OTHER PUBLICATIONS

Correlated Solutions, "Principle of Digital Image Correlation," 2013 (http://correlatedsolutions.com/digital-image-correlation/).
(Continued)

*Primary Examiner* — Jaime Figueroa
(74) *Attorney, Agent, or Firm* — Mintz Levin Cohn Ferris Glovsky and Popeo, P.C.

(57) ABSTRACT

A robotic surgical system including a control system that controls the movement of a robotic arm coupled to a tool assembly having an end effector is described. The control system can also assist with controlling either the articulation or rotation of the end effector. Furthermore, the control system can detect and monitor one or more properties (e.g., articulation, rotation, etc.), which can be used by the control system to determine one or more appropriate movement parameters of either the robotic arm (e.g., velocity of movement) or the tool assembly coupled to the robotic arm (e.g., rotational speed of the end effector). The control system can detect any number of characteristics related to the end effector and use such information to control a variety of movement parameters associated with either the robotic arm or the tool assembly.

11 Claims, 13 Drawing Sheets

(51) Int. Cl.
  *B25J 9/04* (2006.01)
  *A61B 34/00* (2016.01)
  *A61B 34/35* (2016.01)

(52) U.S. Cl.
  CPC ......... *A61B 34/35* (2016.02); *A61B 2034/302* (2016.02); *A61B 2034/741* (2016.02); *A61B 2034/742* (2016.02); *A61B 2034/743* (2016.02); *Y10S 901/02* (2013.01); *Y10S 901/15* (2013.01)

(58) Field of Classification Search
  CPC ...... A61B 34/35; A61B 2034/305; B25J 9/04; Y10S 901/02; Y10S 901/15
  USPC .................................................. 700/245, 250
  See application file for complete search history.

(56) References Cited

U.S. PATENT DOCUMENTS

| | | | |
|---|---|---|---|
| 8,882,792 B2 | 11/2014 | Dietz et al. | |
| 8,915,842 B2 | 12/2014 | Weisenburgh, II et al. | |
| 8,931,682 B2 | 1/2015 | Timm et al. | |
| 8,945,098 B2 | 2/2015 | Seibold et al. | |
| 9,226,761 B2* | 1/2016 | Burbank | A61B 17/07207 |
| 2008/0081948 A1 | 4/2008 | Weisenburgh et al. | |
| 2010/0332031 A1 | 12/2010 | Itkowitz et al. | |
| 2011/0118709 A1 | 5/2011 | Burbank | |
| 2011/0118778 A1* | 5/2011 | Burbank | A61B 17/07207 606/205 |
| 2013/0282052 A1 | 10/2013 | Aranyi et al. | |
| 2014/0005718 A1 | 1/2014 | Shelton, IV et al. | |
| 2014/0276954 A1* | 9/2014 | Hourtash | B25J 9/1607 606/130 |
| 2015/0100066 A1* | 4/2015 | Kostrzewski | A61B 34/30 606/130 |
| 2015/0142047 A1* | 5/2015 | Burbank | A61B 17/07207 606/205 |
| 2015/0293596 A1* | 10/2015 | Krausen | B25J 13/02 606/130 |
| 2016/0106429 A1* | 4/2016 | Burbank | A61B 17/07207 227/180.1 |
| 2017/0000572 A1* | 1/2017 | Moctezuma De La Barrera | A61B 34/32 |

OTHER PUBLICATIONS

U.S. Appl. No. 15/131,963 entitled "Method for Operating a Surgical Instrument" filed Apr. 18, 2016.
U.S. Appl. No. 15/177,430 entitled "Surgical Instrument With User Adaptable Techniques", filed Jun. 9, 2016.
International Search Report for PCT Application No. PCT/US2017/046452 dated Nov. 14, 2017 (6 pages).

* cited by examiner

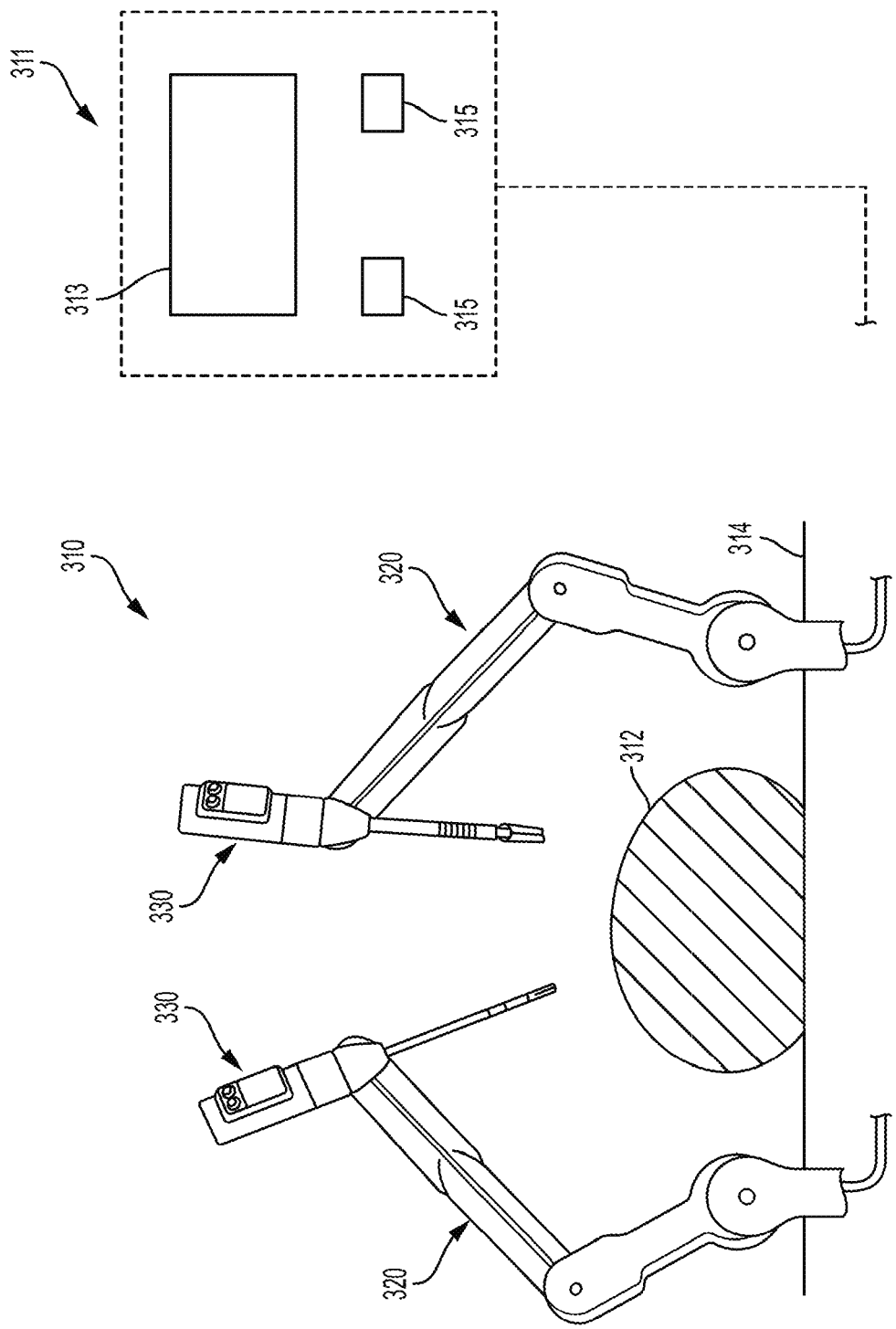

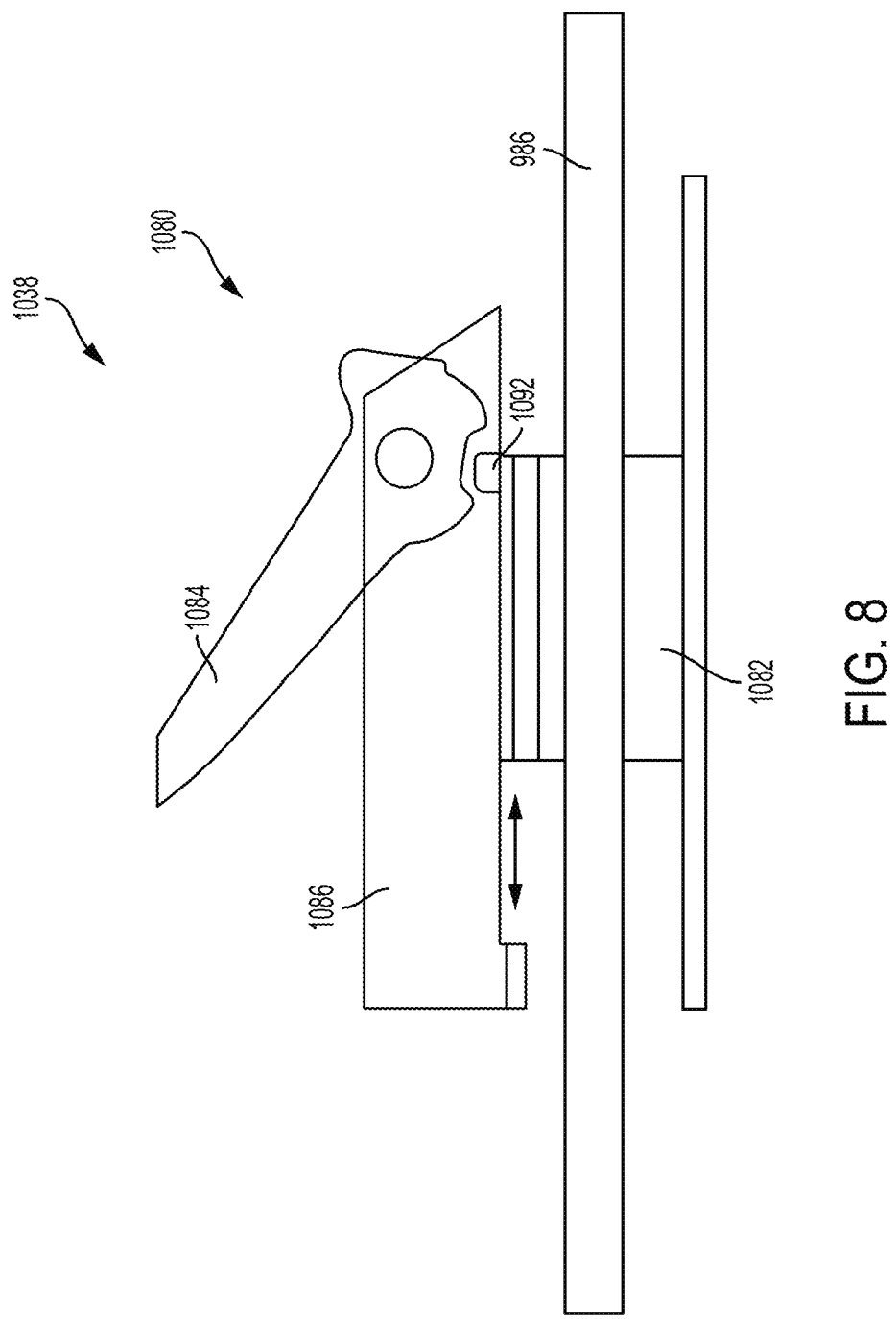

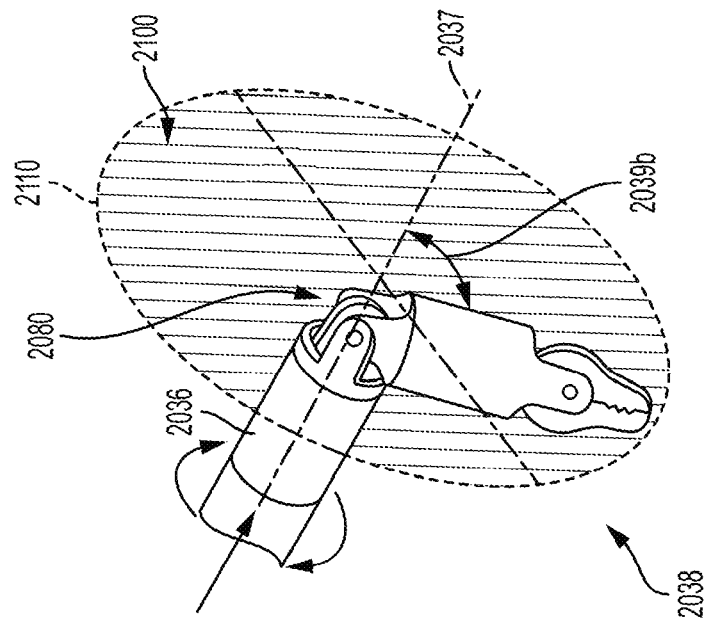
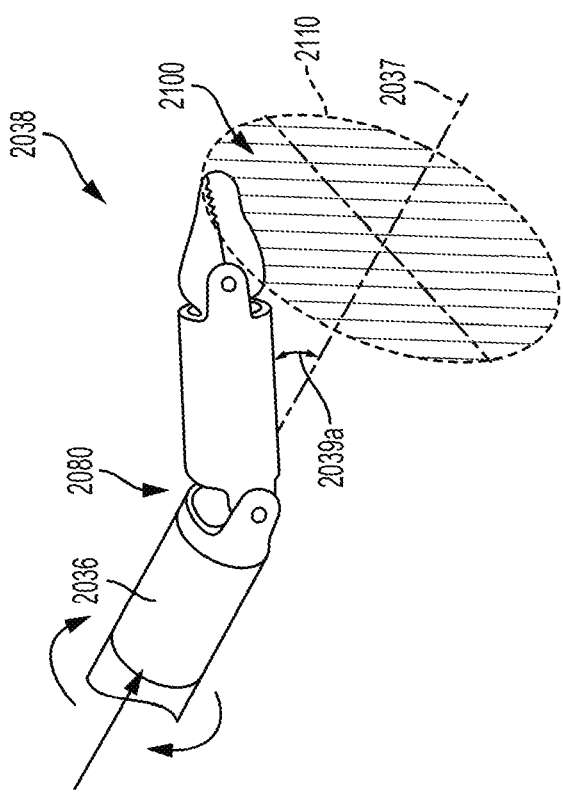
FIG. 9A
FIG. 9B

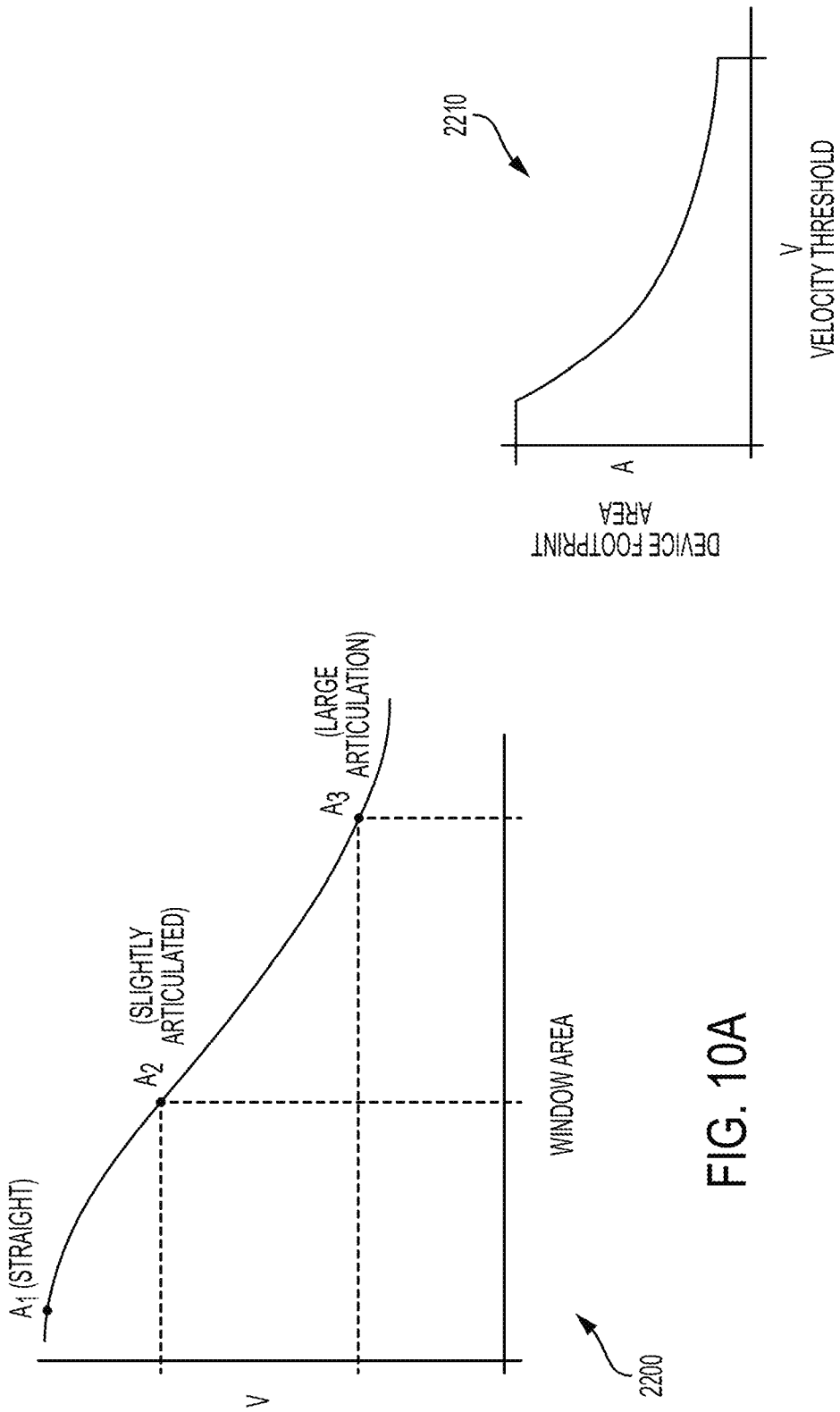

CONTROL OF THE RATE OF ACTUATION OF TOOL MECHANISM BASED ON INHERENT PARAMETERS

FIELD OF THE INVENTION

Methods and devices are provided for robotic surgery, and in particular control system and methods for controlling movement of a robotic tool based on a configuration or property of an end effector of the robotic tool are provided.

BACKGROUND OF THE INVENTION

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Although traditional minimally invasive surgical instruments and techniques have proven highly effective, newer systems may provide even further advantages. For example, traditional minimally invasive surgical instruments often deny the surgeon the flexibility of tool placement found in open surgery. Difficulty is experienced in approaching the surgical site with the instruments through the small incisions. Additionally, the added length of typical endoscopic instruments often reduces the surgeon's ability to feel forces exerted by tissues and organs on the end effector. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity and sensitivity of endoscopic tools has been found to be an impediment in the increased use of minimally invasive surgery.

Over the years a variety of minimally invasive robotic systems have been developed to increase surgical dexterity as well as to permit a surgeon to operate on a patient in an intuitive manner. Telesurgery is a general term for surgical operations using systems where the surgeon uses some form of remote control, e.g., a servomechanism, or the like, to manipulate surgical instrument movements, rather than directly holding and moving the tools by hand. In such a telesurgery system, the surgeon is typically provided with an image of the surgical site on a visual display at a location remote from the patient. The surgeon can typically perform the surgical procedure at the location remote from the patient whilst viewing the end effector movement on the visual display during the surgical procedure. While viewing typically a three-dimensional image of the surgical site on the visual display, the surgeon performs the surgical procedures on the patient by manipulating master control devices at the remote location, which master control devices control motion of the remotely controlled instruments.

While significant advances have been made in the field of robotic surgery, there remains a need for improved methods, systems, and devices for use in robotic surgery.

SUMMARY OF THE INVENTION

Aspects of the current subject matter include a robotic surgical system having a control system that can detect and monitor a variety of configurations and properties (e.g., rotational speed, etc.) associated with a part of a tool assembly (e.g., end effector) for controlling a movement property (e.g., velocity) of either a robotic arm of the surgical system or the tool assembly coupled to the robotic arm.

In one aspect, a robotic surgical system is described that includes a robotic arm having a proximal end configured to be coupled to a support and having a driver at a distal end of the robotic arm. The driver can include one or more motors. In addition, the robotic surgical system can include a tool assembly having a housing configured to releasably couple to the driver. The housing can include a first actuator and a second actuator that are each actuated by at least one of the one or more motors. The tool assembly can further include a shaft extending distally from the housing and operatively coupled to the first actuator such that actuation of the first actuator causes the shaft to rotate. In addition, the tool assembly can include an end effector pivotally coupled to a distal end of the shaft. The end effector can be configured to pivot upon actuation of the second actuator to form an angle between a first longitudinal axis of the end effector and a second longitudinal axis of the shaft. Additionally, the robotic surgical system can include a control system configured to control, based on the angle formed from a current position of the end effector, a velocity of movement of the robotic arm. The velocity of movement can be related to the angle. In some implementations, the control system can further control the velocity of movement of the robotic arm based on a rotational velocity of the shaft where the velocity of movement is related to the rotational velocity of the shaft.

In another aspect, a robotic surgical system is described that includes a robotic arm having a proximal end configured to be coupled to a support and having a driver at a distal end of the robotic arm. The robotic arm can be movable relative to the support. In addition, the robotic surgical system can include a tool assembly having a housing configured to releasably couple to the driver. The housing can include an actuator that is actuated by a motor associated with the driver. The tool assembly can further include a shaft extending from the housing and an end effector pivotally coupled to a distal end of the shaft and configured to pivot in response to the actuator thereby defining at least one window area. Each of the at least one window area can have a radius that is equal to a distance between a distal end of the end effector and a longitudinal axis of the shaft. Furthermore, the robotic surgical system can include a control system configured to control, based on the radius of a current position of the end effector, a velocity of movement of the robotic arm. The velocity of movement can be related to the radius. In some implementations, the control system can further control the velocity of movement of the robotic arm based on a moment of inertia of the end effector. The velocity of movement can be related to the moment of inertia of the end effector. In some implementations, the moment of inertia is defined by one or more of a mass of the end effector, a speed of rotation of the end effector, and the distance between the distal end of the end effector and the longitudinal axis of the shaft.

In another interrelated aspect of the current subject matter, a method includes determining a first articulation angle of an end effector located at a distal end of a shaft of a tool assembly, the tool assembly being coupled to a robotic arm of a robotic surgical system. The method can further include setting, based on the determined first articulation angle, a first maximum velocity of movement of the robotic arm. In addition, the method can include articulating the end effector and determining a second articulation angle of the end effector where the second articulation angle is larger than the first articulation angle. The method can further include setting, based on the determined second articulation angle, a second maximum velocity of movement of the robotic arm, the second maximum velocity of movement being less than the first maximum velocity of movement. In some implementations, the first and second articulation angles can be each defined by an angle formed between the end effector and a longitudinal axis of the shaft. In some implementations, the method includes rotating the end effector about a longitudinal axis of the shaft and setting, based on the rotating of the end effector, a third maximum velocity of movement of the robotic arm, with the third maximum velocity of movement being less than the second maximum velocity of movement.

Another method can include determining a first window area defined by a distal end of an end effector rotated about a longitudinal axis of a shaft of a tool assembly. The tool assembly can be coupled to a robotic arm of a robotic surgical system. In addition, the method can include setting, based on the determined first window area, a first maximum velocity of movement of the robotic arm. The method can further include articulating the end effector and determining a second window area defined by the distal end of the end effector rotated about a longitudinal axis of the shaft, with the second window area being larger than the first window area. Furthermore, the method can include setting, based on the determined second window area, a second maximum velocity of movement of the robotic arm, the second maximum velocity of movement being less than the first maximum velocity of movement.

Yet another method can include determining a first moment of inertia of an end effector located at a distal end of a shaft of a tool assembly, with the tool assembly being coupled to a robotic arm of a robotic surgical system. In addition, the method can include setting, based on the determined first moment of inertia, a first maximum velocity of movement of the robotic arm. Additionally, the method can include increasing at least one of a rotational speed of the end effector and an articulation angle of the end effector. The method can further include determining a second moment of inertia of the end effector, the second moment of inertia being larger than the first moment of inertia. Furthermore, the method can include setting, based on the determined second moment of inertia, a second maximum velocity of movement of the robotic arm, the second maximum velocity of movement being less than the first maximum velocity of movement. In some implementations, the moment of inertia is defined by one or more of a mass of the end effector, a speed of rotation of the end effector, and the articulation angle of the end effector The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

The invention will be more fully understood from the following detailed description taken in conjunction with the accompanying drawings, in which:

FIG. 1 illustrates a perspective view of an embodiment of a surgical robotic system that includes a patient-side portion and a user-side portion.

FIG. 8 illustrates a portion of the end effector of FIG. 7.

FIG. 9A illustrates another embodiment of end effector shown articulated at a first angle relative to a longitudinal axis of the shaft.

FIG. 9B illustrates the end effector of FIG. 9A shown articulated at a second angle relative to the longitudinal axis of the shaft.

FIG. 10A illustrates a first graph showing a decrease in velocity of movement of a robotic arm as the articulation of the end effector increases.

FIG. 10B illustrates a second graph showing a decrease in a maximum allowable velocity of movement of the robotic arm as a footprint of the end effector increases, where the footprint can include at least one of an articulation of the end effector and a shaft rotation.

DETAILED DESCRIPTION OF THE INVENTION

Figure 3:
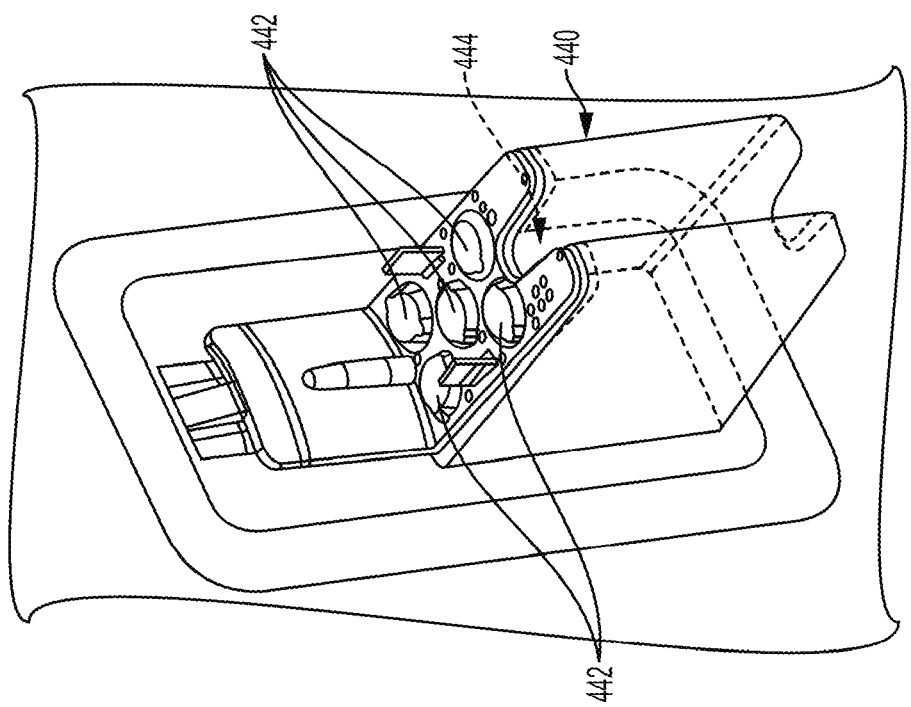
FIG. 3 illustrates an embodiment of a tool driver of the robotic arm of FIG. 2.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

In general, a control system of a surgical robotic system is described that can assist with performing surgical procedures on a patient. Such procedures can require the robotic surgical system to move a surgical arm and manipulate a tool assembly coupled to the robotic arm. For example, a tool assembly can include an end effector positioned at a distal end of a shaft. The end effector can be articulated and rotated about the shaft in order to reach and manipulate tissue at a surgical site. In addition, the robotic arm can assist with moving and positioning the tool assembly relative to the surgical site. Such movements made by the tool assembly and/or robotic arm can result in damage to either the tool assembly or patient if the wrong move is made or a move is made too quickly. Furthermore, such damage can be increased depending on a configuration or property of the tool assembly. For example, if caused to rotate about the shaft, an end effector having a large articulation angle relative to the shaft can potentially cause more tissue damage to a patient compared to an end effector that is straight. As such, in order to reduce the occurrence and severity of tissue damage to a patient, the control system controls at least one movement property (e.g., a velocity threshold, a movement velocity, etc.) of the robotic surgical system and tool assembly based on at least one property associated with the end effector (e.g., articulation, rotation, etc.). The control system can determine and monitor any number of configurations and inherent properties associated with the robotic surgical system and/or tool assembly (e.g., end effector), which can be used by the control system to determine one or more appropriate movement properties (e.g., rotation, velocity, etc.) associated with the robotic surgical system and/or tool assembly, as will be discussed in greater detail below. Furthermore, such control by the control system can allow the robotic system to move in smooth and/or predictable ways, which can emulate natural motion of human control and provide safety features that, for example, reduce tool assembly and/or robotic arm collisions.

As indicated above, in one embodiment the systems, devices, and methods disclosed herein can be implemented using a robotic surgical system. As will be appreciated by a person skilled in the art, electronic communication between various components of a robotic surgical system can be wired or wireless. A person skilled in the art will also appreciate that all electronic communication in the system can be wired, all electronic communication in the system can be wireless, or some portions of the system can be in wired communication and other portions of the system can be in wireless communication.

FIG. 1 is a perspective view of one embodiment of a surgical robotic system 300 that includes a patient-side portion 310 that is positioned adjacent to a patient 312, and a user-side portion 311 that is located a distance from the patient, either in the same room and/or in a remote location. The patient-side portion 310 generally includes one or more robotic arms 320 and one or more tool assemblies 330 that are configured to releasably couple to a robotic arm 320. The user-side portion 311 generally includes a vision system 313 for viewing the patient 312 and/or surgical site, and a control system 315 for controlling the movement of the robotic arms 320 and each tool assembly 330 during a surgical procedure.

The control system 315 can have a variety of configurations and it can be located adjacent to the patient, e.g., in the operating room, remote from the patient, e.g., in a separate control room, or it can be distributed at two or more locations. For example, a dedicated system control console can be located in the operating room, and a separate console can be located in a remote location. The control system 315 can include components that enable a user to view a surgical site of a patient 312 being operated on by the patient-side portion 310 and/or to control one or more parts of the patient-side portion 310 (e.g., to perform a surgical procedure at the surgical site 312). In some embodiments, the control system 315 can also include one or more manually-operated input devices, such as a joystick, exoskeletal glove, a powered and gravity-compensated manipulator, or the like. These input devices can control teleoperated motors which, in turn, control the movement of the surgical system, including the robotic arms 320 and tool assemblies 330.

The patient-side portion can also have a variety of configurations. As depicted in FIG. 1, the patient-side portion 310 can couple to an operating table 314. However, in some embodiments, the patient-side portion 310 can be mounted to a wall, to the ceiling, to the floor, or to other operating room equipment. Further, while the patient-side portion 310 is shown as including two robotic arms 320, more or fewer robotic arms 320 may be included. Furthermore, the patient-side portion 310 can include separate robotic arms 320 mounted in various positions, such as relative to the surgical table 314 (as shown in FIG. 1). Alternatively, the patient-side portion 310 can include a single assembly that includes one or more robotic arms 320 extending therefrom.

Figure 2:
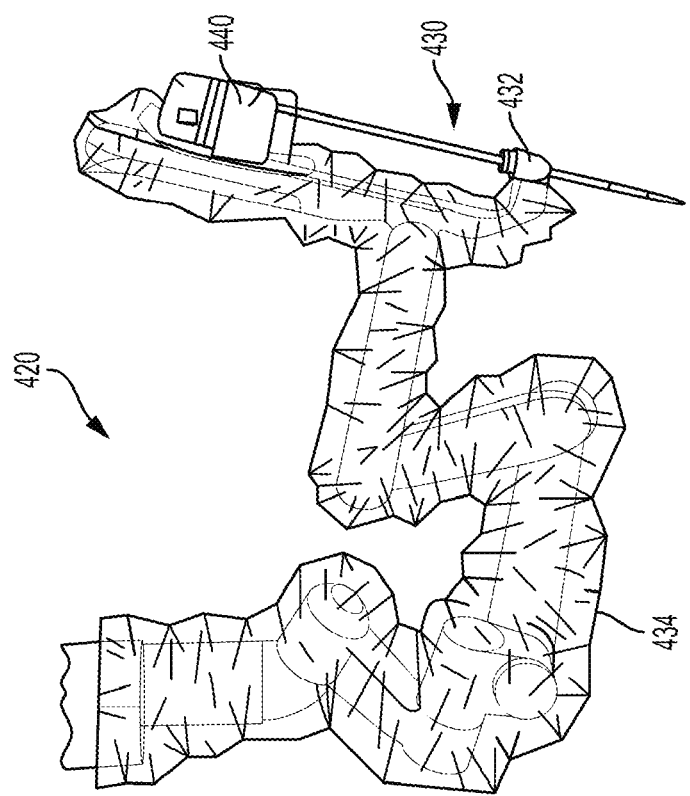
FIG. 2 illustrates an embodiment of a robotic arm of the surgical robotic system of FIG. 1 with a tool assembly releasably coupled to the robotic arm.

FIG. 2 illustrates one embodiment of a robotic arm 420 and a tool assembly 430 releasably coupled to the robotic arm 420. The robotic arm 420 can support and move the associated tool assembly 430 along one or more mechanical degrees of freedom (e.g., all six Cartesian degrees of freedom, five or fewer Cartesian degrees of freedom, etc.).

The robotic arm 420 can include a tool driver 440 at a distal end of the robotic arm 420, which can assist with controlling features associated with the tool assembly 430. The robotic arm 420 can also include an entry guide 432 (e.g., a cannula mount or cannula) that can be a part of or removably coupled to the robotic arm 420, as shown in FIG. 2. A shaft 436 of the tool assembly 430 can be inserted through the entry guide 430 for insertion into a patient.

In order to provide a sterile operation area while using the surgical system, a barrier 434 can be placed between the actuating portion of the surgical system (e.g., the robotic arm 420) and the surgical instruments (e.g., the tool assembly 430). A sterile component, such as an instrument sterile adapter (ISA), can also be placed at the connecting interface between the tool assembly 430 and the robotic arm 420. The placement of an ISA between the tool assembly 430 and the robotic arm 420 can ensure a sterile coupling point for the tool assembly 430 and the robotic arm 420. This permits removal of tool assemblies 430 from the robotic arm 420 to exchange with other tool assemblies 430 during the course of a surgery without compromising the sterile surgical field.

FIG. 3 illustrates the tool driver 440 in more detail. As shown, the tool driver 440 includes one or more motors, e.g., five motors 442 are shown, that control a variety of movements and actions associated with the tool assembly 430, as will be described in greater detail below. For example, each motor 442 can couple to and/or interact with an activation feature (e.g., gear) associated with the tool assembly 430 for controlling one or more actions and movements that can be performed by the tool assembly 430, such as for assisting with performing a surgical operation. The motors 442 are accessible on the upper surface of the tool driver 440, and thus the tool assembly is configured to mount on top of the tool driver 440 to couple thereto. The tool driver 440 also includes a shaft-receiving channel 444 formed in a sidewall thereof for receiving the shaft of the tool assembly 430. In other embodiments, the shaft can extend through on opening in the tool driver 440, or the two components can mate in various other configurations.

Figure 4:
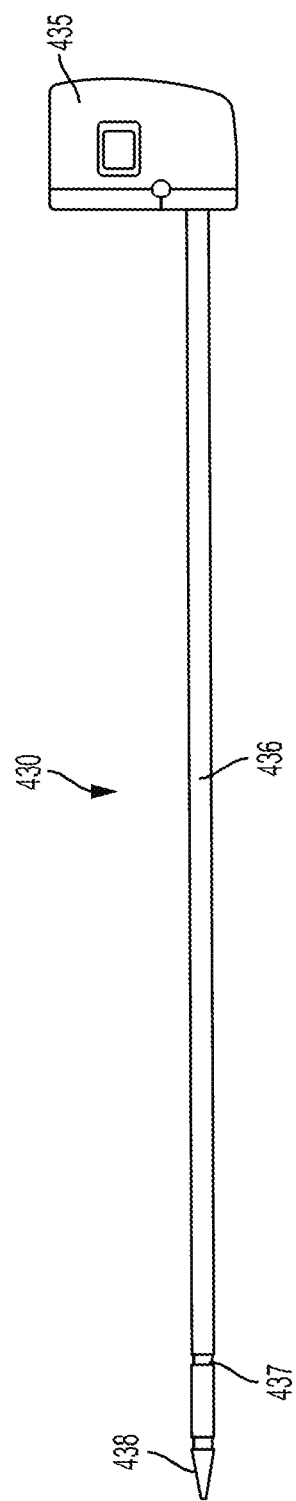
FIG. 4 illustrates the tool assembly of FIG. 2 uncoupled from the robotic arm, the tool assembly including a shaft extending from a puck at a proximal end and having an end effector located at a distal end of the shaft.

FIG. 4 illustrates the tool assembly 430 uncoupled from the robotic arm 420. The tool assembly 430 includes a housing or puck 435 coupled to a proximal end of a shaft 436 and an end effector 438 coupled to a distal end of the shaft 436. The end effector can include a pair of jaws, such as a second jaw that pivots relative to a first jaw. The second jaw can pivot between a closed position where the pair of jaws are configured to engage tissue therebetween and an open position where the pair of jaws are configured to receive tissue therebetween. A cartridge that holds staples can be disposed within the first jaw and one or more staples can be delivered to a surgical site upon firing of the end effector to staple tissue engaged therebetween. The puck 435 can include coupling features that assist with releasably coupling the puck 435 to the tool driver 440 of the robotic arm 420. The puck 435 can include gears and/or actuators that can be actuated by the one or more motors 442 in the driver 440, as will be described in greater detail below. The gears and/or actuators in the puck 435 can control the operation of various features associated with the end effector 438 (e.g., clamping, firing, rotation, articulation, energy delivery, etc.), as well as control the movement of the shaft 436 (e.g., rotation of the shaft).

The shaft 436 can be fixed to the puck 435, or it can be releasably coupled to the puck 435 such that the shaft 436 can be interchangeable with other shafts. This can allow a single puck 435 to be adaptable to various shafts 436 having different end effectors 438. The shaft 436 can include actuators and connectors that extend along the shaft and assist with controlling the actuation and/or movement of the end effector 438 and/or shaft 436. The shaft 436 can also include one or more joints or wrists 437 that allow a part of the shaft 436 or the end effector 438 to articulate relative to the longitudinal axis of the shaft 436. This can allow for fine movements and various angulation of the end effector 438 relative to the longitudinal axis of the shaft 436. The end effector 438 can include any of a variety of surgical tools, such as a stapler, a clip applier, forceps, a needle driver, a cautery device, a cutting tool, a pair of jaws, an imaging device (e.g., an endoscope or ultrasound probe), or a combined device that includes a combination of two or more various tools.

Figure 5:
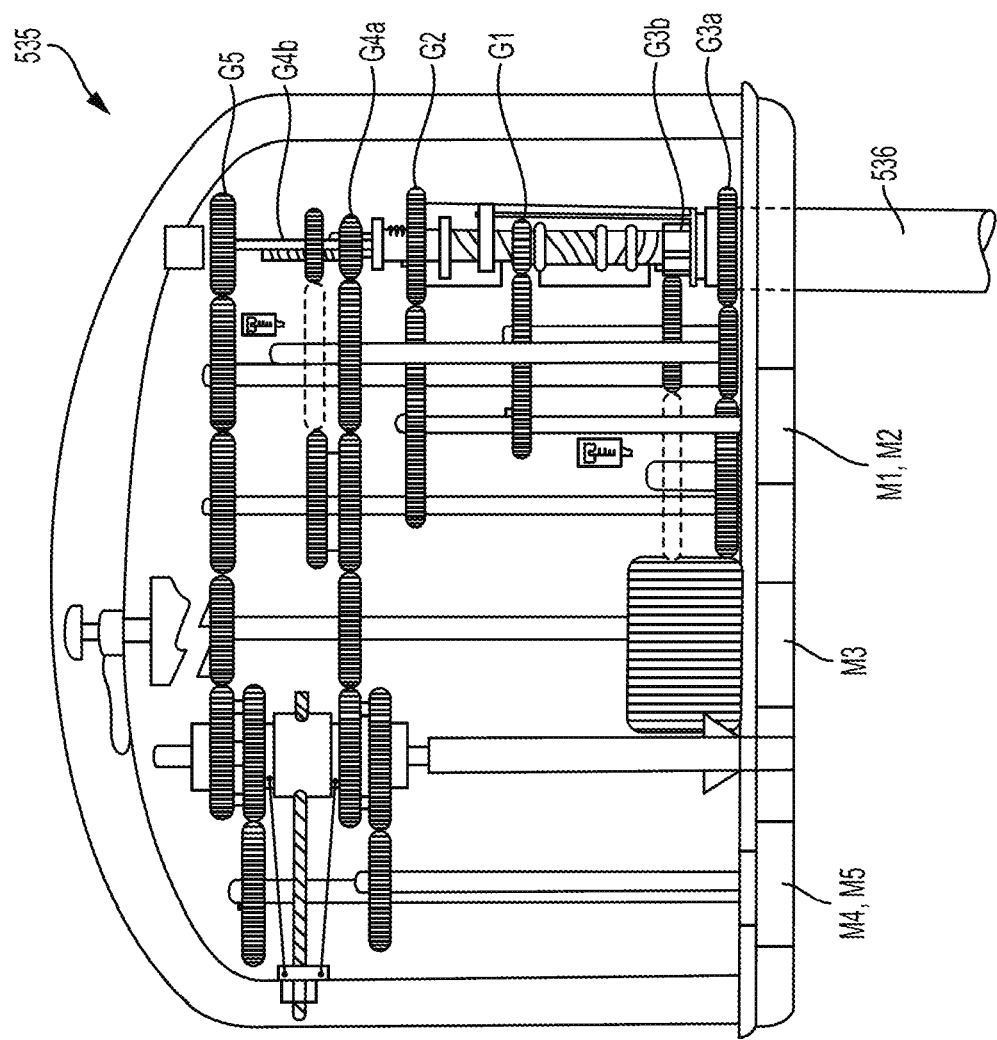
FIG. 5 illustrates an embodiment of the puck of the tool assembly of FIG. 4.

FIG. 5 illustrates the puck 435 and a proximal end of a shaft 436 extending from the puck 435 in more detail. As shown in FIG. 5, the puck 435 includes a plurality of actuation gears and gear shafts that can be either directly or indirectly controlled to any one of the motors 442 associated with the driver 440. For example, as shown in FIG. 5, the puck 435 is configured to couple to five motors at the locations indicated by reference numbers M1, M2, M3, M4, and M5. In this embodiment, puck 435 includes first and second articulation gears G1, G2 that are coupled respectively to the first and second motors M1, M2 via a series of one or more additional gears and shafts. Actuation of the first and second motors M1, M2 will rotate the articulation gears G1, G2, which in turn cause linear movement of an articulation cable in a proximal or distal direction to thereby cause articulation of the end effector 438 in desired left and right directions. The puck 435 also includes a shaft rotation gear G3$a$ that is coupled to the third motor M3 via a series of one or more additional gears and shafts. Actuation of the third motor M3 will thus rotate the shaft rotation gear G3$a$ thereby causing rotation of the shaft 436 of the tool assembly 430. The third motor M3 can also be configured to shift and to couple, via a series of one or more additional gears and shafts, to a head rotation gear G3$b$ which will cause rotation of the end effector 438 relative to the shaft 436. The puck 435 further includes a firm close gear G4$a$ that is coupled to the fourth motor M4 via a series of one or more additional gears and shafts. Actuation of the fourth motor M4 will rotate the firm close gear G4$a$ to cause linear translation of a drive screw to firmly close the jaws of the end effector 438. The puck 435 further includes a quick close gear G4$b$ that can also couple to the fourth motor M4 via a series of one or more additional gears and shafts. When motor M4 is shifted into engagement with the quick close gear G4$b$, actuation of the fourth motor M4 will rotate the quick close gear G4$b$ to cause linear translation of a quick close cable to quickly close the jaws of the end effector 438. Finally, the illustrated puck 435 includes a firing gear G5 that is coupled to the fifth motor M5 via a series of one or more additional gears and shafts. Actuation of the fifth motor M5 will rotate the firing gear G5, thereby driving a lead screw linearly to advance a sled through the end effector 438, as will be discussed in more detail below.

Figure 6:
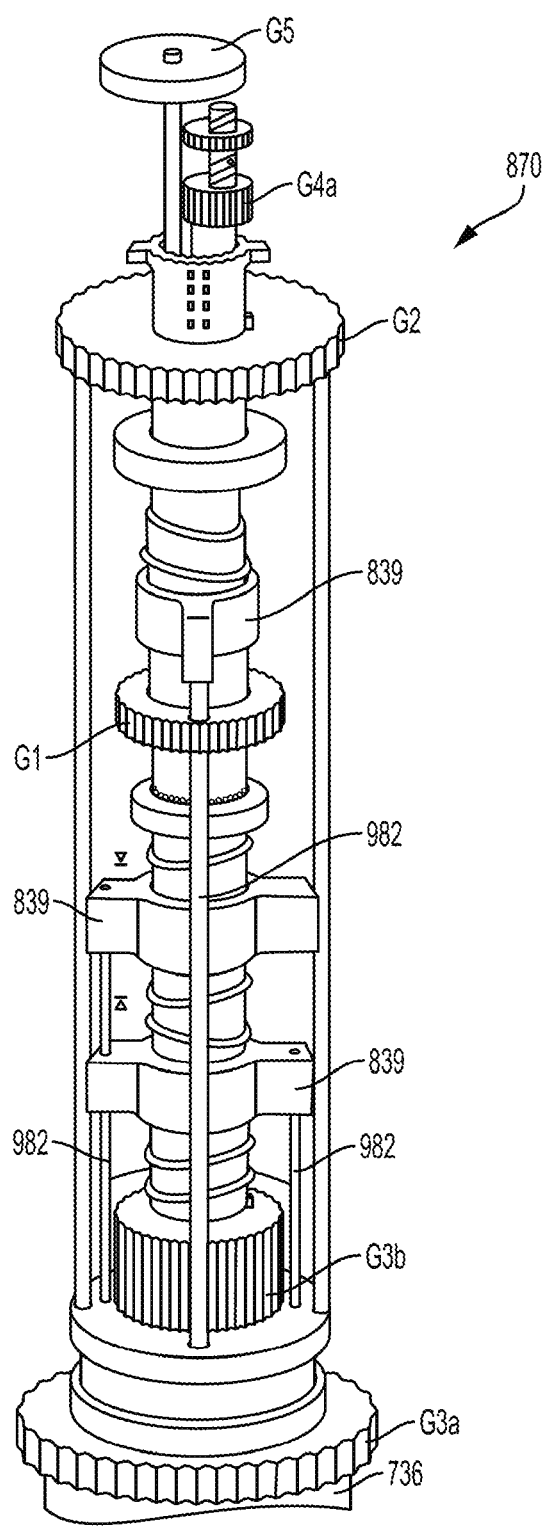
FIG. 6 illustrates an embodiment of an actuation assembly of the puck of FIG. 5.
Figure 7:
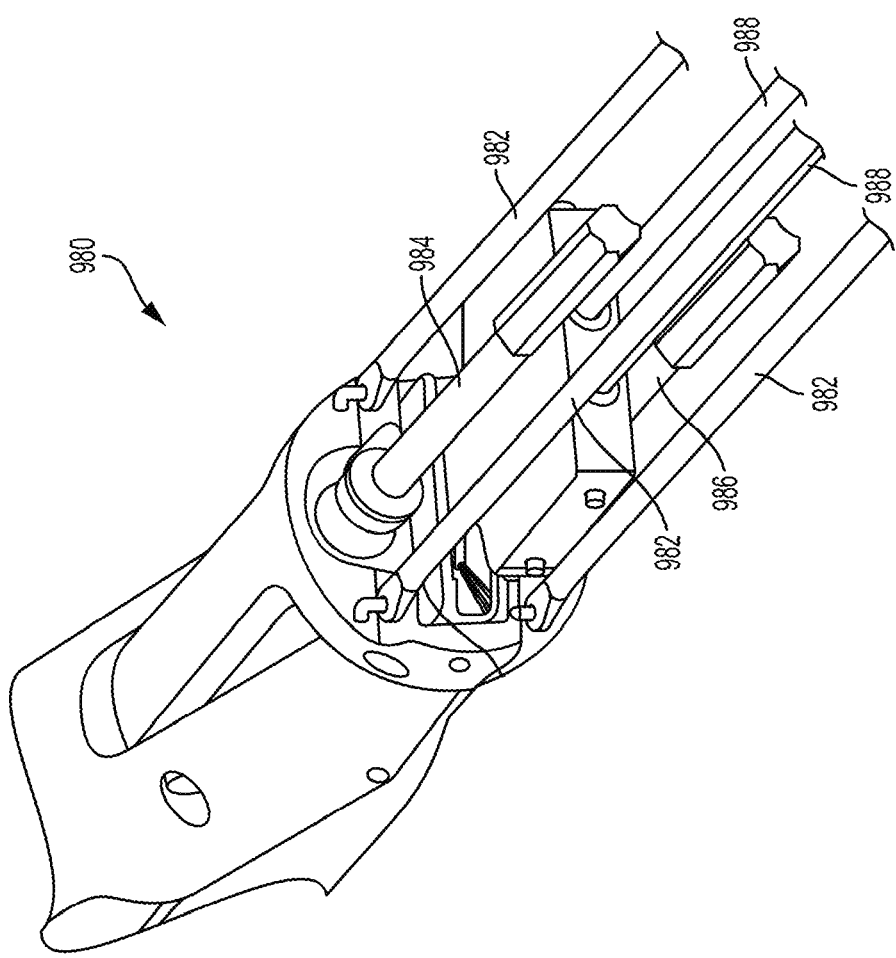
FIG. 7 illustrates an embodiment of actuation shafts extending from a wrist located just proximal of the end effector of FIG. 4.

FIG. 6 illustrates the actuation assembly 870 components of the puck 435 of FIG. 5. As shown and indicated above, each of the gears G1-G5 is coupled to an actuation shaft that extends from the actuation assembly 870 and along the shaft 436 of the tool assembly 430, such as for controlling the movements of the end effector. FIG. 7 illustrates a distal end of the actuation shafts extending from a wrist 980 located just proximal of the end effector 438. The wrist 980 can allow for fine movements and angulation of the end effector 438 relative to the proximal end of the shaft 436. As shown in FIG. 7, the wrist 980 includes four articulation cables 982 that are spaced around a perimeter of the wrist 980. When actuated (e.g., pushed, pulled, rotated), the articulation cables 982 will cause articulation of the end effector 438 (e.g., movement up, down, left, right, and combinations thereof) relative to the proximal end of the shaft 436. The articulation cables 982 are connected to the articulation couplers 839, shown in FIG. 6, that are driven proximally and distally when the articulation gears G1, G2 are actuated by the first and second motors M1, M2. The wrist 980 also includes an upper rotary driver 984 that when actuated can cause the pair of jaws of the end effector 438 to firmly close. The upper rotary driver 984 is coupled to the firm close gear G4$a$ shown in FIG. 6 such that rotation of the firm close gear G4a by the motor M4 causes rotation of the rotary driver 984. The wrist 980 can also include a lower rotary driver 986 that when actuated can cause movement of a sled located at the end effector 438. The lower rotary driver 986 is coupled to the firing gear G5 shown in FIG. 6 and it likewise rotates in response to rotation of the firing gear G5. The illustrated wrist 980 further includes a linear pull cable 988 that is coupled to the quick close gear G4b shown in FIG. 6 and that moves linearly in a proximal direction to cause rapid close of the pair of jaws.

FIG. 8 illustrates a portion of an end effector 1038 having a knife actuation assembly 1080 that includes a drive member 1082, a knife 1084, a knife sled 1086, and a lead screw or rotary driver 986. The drive member 1082 includes internal threads that are threadably coupled with the rotary driver 986. Such coupling can allow drive member 1082 to move along the rotary driver 986 when the rotary driver 986 is rotated. As discussed above, the rotary driver 986 can be actuated at the wrist 980, as shown in FIG. 7, thereby causing rotation of the rotary driver 986 and linear movement of the knife sled 1086 along the rotary driver 986. The rotary driver 986 is coupled to the firing gear G5 shown in FIG. 6. The knife actuation assembly 1080 is configured to orient the knife 1084 in a cutting position when the drive member 1082 pushes the knife sled 1086 along the rotary driver 986 and to stow the knife 1084 when the drive member 1082 is moved proximally relative to the knife sled 1086. In operation, the rotary driver 986 is first rotated to advance the drive member 1082 distally along the rotary driver 986 thereby pushing the knife sled 1086 in the distal direction and angularly orienting the knife 1084 in the cutting position. At the end of the distal movement of the assembly 1080, the direction of rotation of the rotary driver 986 is reversed to retract the drive member 1082 proximally relative to the knife sled 1086, thereby causing the knife 1084 to rotate down into the stowed position, such as via interaction between an interface feature 1092 and the knife 1084.

As discussed above, the end effector can be articulated and rotated about the shaft in order to reach and manipulate tissue at a surgical site. In addition, the robotic arm can assist with moving and positioning the tool assembly relative to the surgical site. Such movements made by the tool assembly and/or robotic arm can result in damage to either the tool assembly or patient if the wrong move is made or a move is made too quickly. Furthermore, such damage or potential damage can be increased depending on a configuration or property of the tool assembly. For example, if caused to rotate about the shaft, an end effector having a large articulation angle relative to the shaft can cause more tissue damage to a patient compared to an end effector that is straight. This can be due to the fact that at a larger articulation angle, more area can be affected as the end effector is rotated about the shaft compared to when the end effector is straight or in-line with the shaft. As such, in order to reduce the occurrence and severity of tissue damage to a patient, at least one inherent property, such as one or more movement properties (e.g., rotation, velocity, etc.) of the robotic surgical system and tool assembly, is controlled based on the configuration of the tooling assembly (e.g., articulation of the end effector).

FIGS. 9A and 9B illustrate an end effector 2038 articulating about a wrist 2080 of a shaft 2036 and rotating about a longitudinal axis 2037 of the shaft 2036. As shown in FIG. 9A, the end effector 2038 can articulate and form a first articulation angle 2039a. As referred to herein, an articulation angle 2039 can be defined as the angle formed between the end effector 2038 (or longitudinal axis of the end effector) and the longitudinal axis 2037 of the shaft 2036. The end effector 2038 can form any number of articulation angles 2039, including a ninety degree articulation angle, as shown in FIG. 9B. The end effector can also be straight or in-line with the longitudinal axis 2037 of the shaft 2036.

The end effector 2038 can rotate about the shaft 2036 (or longitudinal axis 2037 of the shaft) and can do so at a variety of speeds. Such articulation and rotation of the end effector 2038 can be controlled by one or more control features of the robotic surgical system, any one of which can be controlled by a user. As such, the end effector 2038 can articulate to form a variety of articulation angles and can rotate at a variety of speeds.

The robotic surgical system can include a control system (such as the control system 315 shown in FIG. 1) that includes one or more control features that can control movement (e.g., advancement, positioning, etc.) of a robotic arm (such as the robotic arm 320 in FIG. 1). A tool assembly having the end effector at its distal end can be coupled to the robotic arm (see, for example, tool assembly 430 coupled to the robotic arm 420 in FIG. 2). The control system can also assist with controlling either the articulation or rotation of the end effector 2038. Furthermore, the control system can detect one or more properties associated with the end effector 2038 (e.g., articulation angle, rotation, etc.), which can be used by the control system to determine one or more appropriate movement parameters of either the robotic arm (e.g., velocity of movement) or the tool assembly coupled to the robotic arm (e.g., rotational speed of the end effector 2038). The control system can detect any number of characteristics related to the end effector 2038 and use such information to control a variety of movement parameters associated with either the robotic arm or the tool assembly, as will be discussed in greater detail below.

For example, as also shown in FIGS. 9A and 9B, the control system can determine and monitor an affected window area 2100 created by the articulated end effector 2038. The window area 2100 can be defined by the distal end of the end effector 2038 rotating about the longitudinal axis 2037 of the shaft, thereby defining a circumference 2110 of the window area 2100. The greater the articulation angle 2039 of the end effector 2038, the greater the circumference 2110 and window area 2100. The window area 2100 can define an area where the end effector 2038 has the potential to interact with an object, such as tissue of a patient. As such, the greater the articulation angle of the end effector 2038, the greater area of potential interaction and possible greater damage that can be created by the end effector 2038 when moving (e.g., translating, rotating). As such, it can be beneficial for the control system to determine and monitor the window area 2100 created by the configuration of the end effector in order to set and control movements of the robotic arm and tool assembly. Although the window area 2100 is described herein as being defined by the distal end of the end effector 2038 rotating about the longitudinal axis 2037 of the shaft thereby defining a circumference 2110 of the window area 2100, any number of points along the end effector 2038 can be used to define the circumference 2110 of the window area 2100 without departing from the scope of this disclosure.

FIG. 10A illustrates a first graph 2200 showing the velocity of movements of the robotic arm being reduced by the control system as the window area 2100 formed by the end effector 2038 increases. For example, as shown in FIG. 10A, when the end effector 2038 is straight, the velocity of movement of the robotic arm is greatest. As the window area 2100 increases as a result of the articulation angle of the end effector increasing, the control system decreases the velocity of movement of the robotic arm. As the window area 2100 decreases as a result of the articulation angle of the end effector decreasing, the control system increases the velocity of movement of the robotic arm. Such changes in the velocity of movement (e.g., increase or decrease) can thus be related to the window area formed by the end effector and such relationship can be linear (e.g., inversely proportional) or nonlinear. In some implementations, the control system sets a threshold or maximum velocity that the robotic arm can move based on the articulation angle 2039 or window area 2100 of the end effector 2038. As such, the control system can either set a maximum velocity or directly control the velocity based on the articulation angle 2039 or window area 2100 of the end effector.

FIG. 10B illustrates a second graph 2210 showing the control system increasing the maximum velocity (or velocity threshold) as a footprint area decreases. The footprint area can be similar to the window area 2100 in that it can include an area defined by the articulation of the end effector 2038. However, the footprint area can also include the rotational speed of the end effector 2038. Due to the potential damage that can be made within the window area 2100 and the footprint area, the control system sets the velocity of movement of the associated robotic arm such that as either the window area 2100 or the rotational speed of the end effector (i.e., a factor of the footprint area) increase, the velocity or maximum allowable velocity is decreased. This can at least reduce the extent of damage created by the end effector if the end effector is moved in an undesired area. In addition, as either the window area 2100 or the rotational speed of the end effector (i.e., a factor of the footprint area) decrease, the velocity or maximum allowable velocity is increased. Such changes in the maximum allowable velocity of movement (e.g., increase or decrease) can thus be related to the footprint area defined by the end effector and such relationship can be linear or nonlinear.

Figure 11:
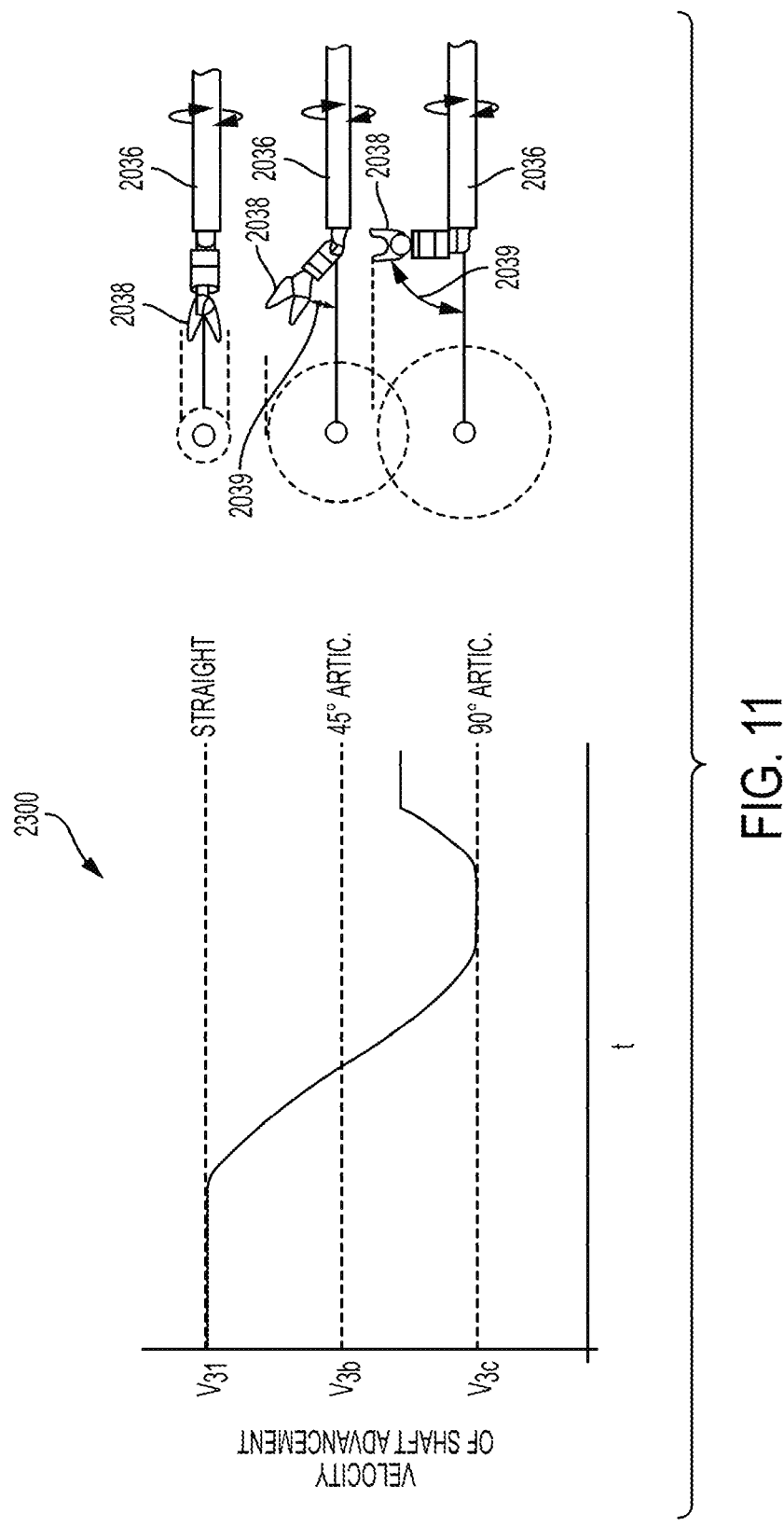
FIG. 11 illustrates a third graph that shows an example of the differences in velocity thresholds of shaft movements at various articulation angles of the end effector while rotating about the shaft over time.

FIG. 11 shows a third graph 2300 that illustrates an example of the differences in velocity thresholds of shaft 2036 movements (e.g., as a result of robotic arm movements) at various articulation angles 2039 of the end effector 2038 while rotating about the shaft 2036 over time. As shown in FIG. 11, the velocity or threshold velocity of shaft advancement (or movement) is reduced as the end effector articulates from straight to a 45 degree angle, and then further reduced when the end effector 2038 articulates to a 90 degree angle. Additionally, the velocity or threshold velocity of shaft advancement (or movement) is increased as the end effector articulates from a 90 degree angle to a 45 degree angle, and then further increased when the end effector 2038 articulates to being straight. Such changes in the velocity or threshold velocity of shaft movement (e.g., increase or decrease) can thus be related to the articulation angle of the end effector and such relationship can be linear or nonlinear. The end effector 2038 can rotate at various speeds while either straight or forming an angle relative to the shaft 2036.

Figure 12:
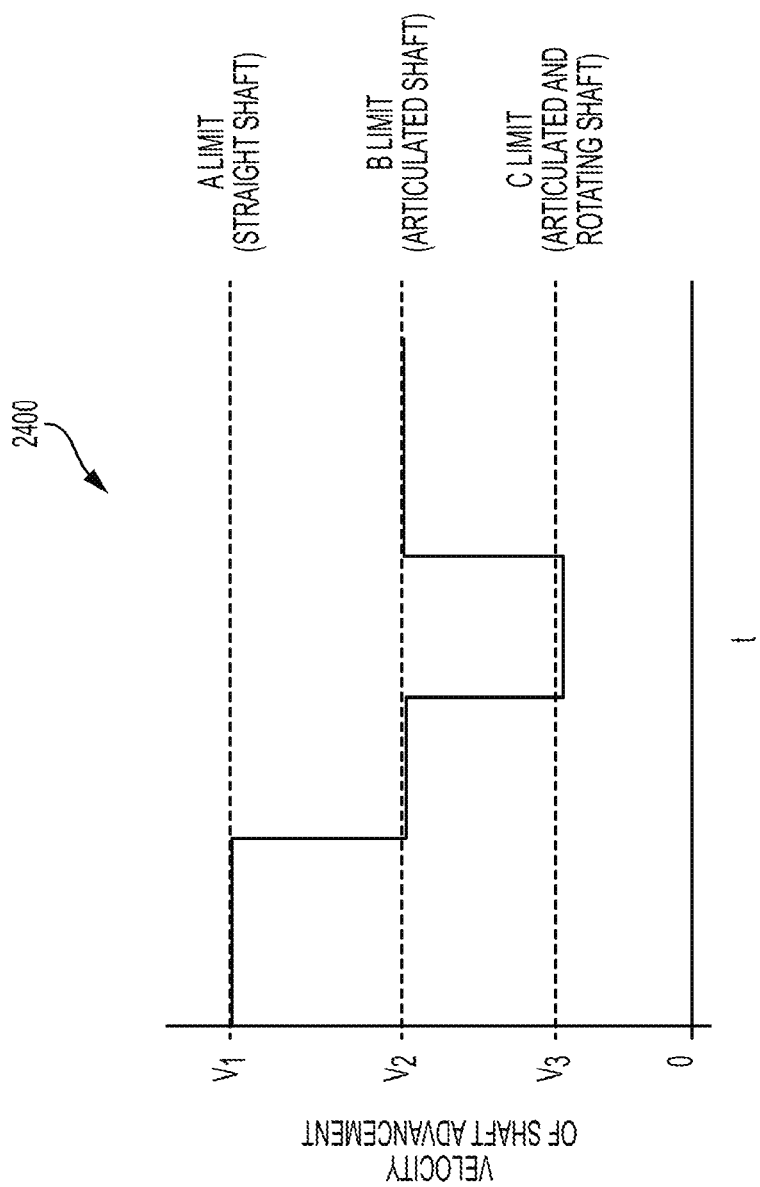
FIG. 12 illustrates a fourth graph that shows an example of the differences in velocity thresholds of shaft advancement (or movement) based on one or more factors associated with the end effector over time.

FIG. 12 shows a fourth graph 2400 that illustrates an example of the differences in velocity thresholds of shaft advancement (or movement) based on one or more factors associated with the end effector 2038 over time. As shown in FIG. 12, the velocity or threshold velocity of movement of the shaft 2036 is reduced as the end effector 2038 moves from having a straight configuration to being articulated. As also shown in FIG. 12, the velocity or threshold velocity of movement of the shaft 2036 is further reduced as the end effector 2038 rotates in the articulated configuration. As such, the control system can determine and monitor both the articulation and rotation of the end effector 2038 to set the velocity or velocity threshold of movement of the robotic arm and shaft 2036. Furthermore, the control system can set the velocity or velocity threshold to be lower either as the articulation angle 2039 of the end effector 2038 increases or when the end effector 2038 rotates.

The control system can determine and monitor any number of properties related to the robotic surgical system and/or the tool assembly for setting and/or controlling any number of parameter, such as velocity and velocity thresholds. In some implementations, the control system can control the velocity threshold for speed adjustments and overall stop motion based on one or more properties associated with the end effector 2038. For example, the control system can determine and monitor the moment of inertia of the end effector 2038 to control the velocity threshold and a stop motion. Such control or changes in the velocity threshold and stop motion can thus be related to the moment of inertia of the end effector and such relationship can be linear or nonlinear. The moment of inertia can be defined to include one or more of the mass of the end effector 2038, a rotational speed of the end effector 2038, and a geometry of the end effector 2038 (e.g., the articulation angle 2039 of the end effector 2038). The geometry of the end effector 2038 can include the articulation angle 2039 of the end effector 2038 and/or the distance between the distal end of the end effector 2038 and the longitudinal axis 2037 of the shaft 2036. Furthermore, the moment of inertia can be determined relative to one or more axis about which the end effector is to rotate about. The stop motion can be defined as the amount of time required for the end effector to come to a complete stop based on one or more properties associated with the end effector 2038, such as the current travel speed, rotational speed, moment of inertia, etc. The control system can decrease the velocity threshold as the moment of inertia increases. This can ensure that the end effector stops at a desired location or within a desired distance.

Figure 13A:
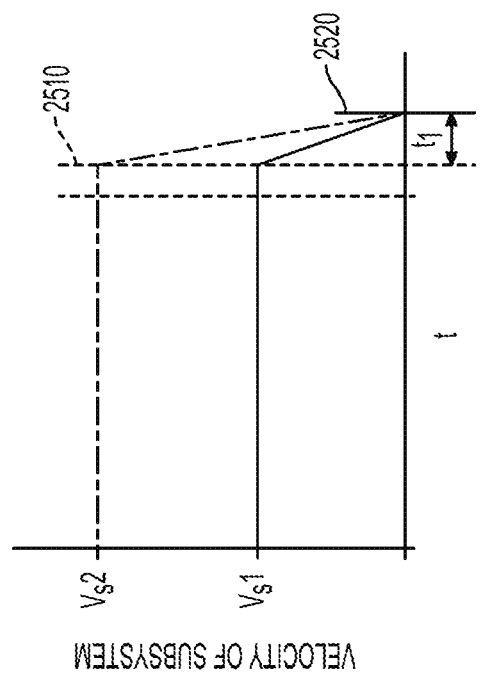
FIGS. 13A and 13B are fifth and sixth graphs, respectively, illustrating an example of the control system affecting the velocity thresholds based on the moment of inertia of the end effector.
Figure 13B:
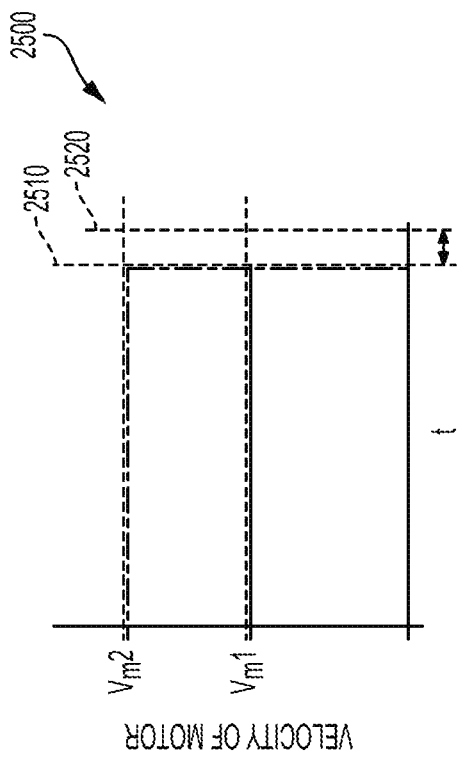

FIGS. 13A and 13B are fifth and sixth graphs, respectively, illustrating an example of the control system affecting the velocity thresholds based on the moment of inertia of the end effector 2038. In the fifth graph 2500 shown in FIG. 13A, a velocity threshold of the motor controlling movement of the robotic arm is shown as being less for an end effector having a greater moment of inertia (e.g., a heavier end effector) compared to an end effector having a smaller moment of inertia. Furthermore, when the motors are turned off (at first line 2510), the velocity of the motor drops to zero almost immediately. However, as shown in the sixth graph 2550 of FIG. 13B, the greater the moment of inertia of the end effector, the lower the rate of change in velocity (as shown by the rate at which the velocity decreases to zero, at line two 2520, after the motor is turned off, at first line 2510). As such, the control system sets a velocity threshold that considers the rate at which the end effector 2038 will decrease in velocity from the threshold velocity to a complete stop. This can ensure that the end effector 2038 is positioned in a desired resting location and does not cause damage to either tissue of a patient or the end effector, such as by overshooting the desired resting location. Although the moment of inertia is described as being related to the end effector, the control system can control the velocity threshold of any part of either the robotic surgical system or tool assembly based on the weight or moment of inertia of any one or more parts of the either the robotic surgical system or tool assembly without departing from the scope of this disclosure.

Figure 14:
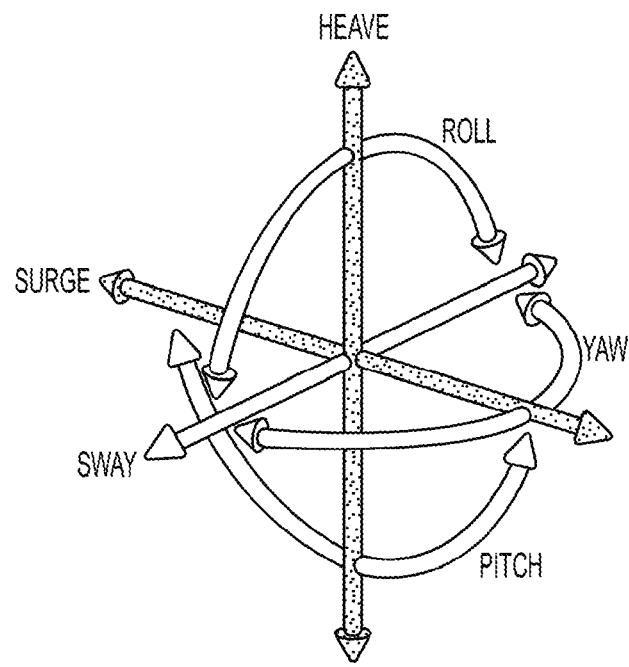
FIG. 14 illustrates movement and rotation along one of the three axes in a Cartesian frame.

There are a number of ways in which to describe the movement of a surgical system, as well as its position and orientation in space. One particularly convenient convention is to characterize a system in terms of its degrees of freedom. The degrees of freedom of a system are the number of independent variables that uniquely identify its pose or configuration. The set of Cartesian degrees of freedom is usually represented by the three translational or position variables, e.g., surge, heave, and sway, and by the three rotational or orientation variables, e.g., Euler angles or roll, pitch, and yaw, that describe the position and orientation of a component of a surgical system with respect to a given reference Cartesian frame. As used herein, and as illustrated in FIG. 14, the term "surge" refers to forward and backward movement, the term "heave" refers to movement up and down, and the term "sway" refers to movement left and right. With regard to the rotational terms, "roll" refers to tilting side to side, "pitch" refers to tilting forward and backward, and "yaw" refers to turning left and right. In a more general sense, each of the translation terms refers to movement along one of the three axes in a Cartesian frame, and each of the rotational terms refers to rotation about one of the three axes in a Cartesian frame.

Although the number of degrees of freedom is at most six, a condition in which all the translational and orientation variables are independently controlled, the number of joint degrees of freedom is generally the result of design choices that involve considerations of the complexity of the mechanism and the task specifications. For non-redundant kinematic chains, the number of independently controlled joints is equal to the degree of mobility for an end effector. For redundant kinematic chains, the end effector will have an equal number of degrees of freedom in Cartesian space that will correspond to a combination of translational and rotational motions. Accordingly, the number of degrees of freedom can be more than, equal to, or less than six.

With regard to characterizing the position of various components of the surgical system and the mechanical frame, the terms "forward" and "rearward" may be used. In general, the term "forward" refers to an end of the surgical system that is closest to the distal end of the input tool, and when in use in a surgical procedure, to the end disposed within a patient's body. The term "rearward" refers to an end of the surgical system farthest from the distal end of the input tool, and when in use, generally to the end farther from the patient.

The terminology used herein is not intended to limit the invention. For example, spatially relative terms, e.g., "superior," "inferior," "beneath," "below," "lower," "above," "upper," "rearward," "forward," etc., may be used to describe one element's or feature's relationship to another element or feature as illustrated in the figures. These spatially relative terms are intended to encompass different positions and orientations of the device in use or operation in addition to the position and orientation shown in the figures. For example, if the device in the figures is turned over, elements described as "inferior to" or "below" other elements or features would then be "superior to" or "above" the other elements or features. Likewise, descriptions of movement along and around various axes include various special device positions and orientations. As will be appreciated by those skilled in the art, specification of the presence of stated features, steps, operations, elements, and/or components does not preclude the presence or addition of one or more other features, steps, operations, elements, components, and/or groups described herein. In addition, components described as coupled may be directly coupled, or they may be indirectly coupled via one or more intermediate components.

There are several general aspects that apply to the various descriptions below. For example, at least one surgical end effector is shown and described in various figures. An end effector is the part of a surgical instrument or assembly that performs a specific surgical function, e.g., forceps/graspers, needle drivers, scissors, electrocautery hooks, staplers, clip appliers/removers, suction tools, irrigation tools, etc. Any end effector can be utilized with the surgical systems described herein. Further, in exemplary embodiments, an end effector can be configured to be manipulated by a user input tool. The input tool can be any tool that allows successful manipulation of the end effector, whether it be a tool similar in shape and style to the end effector, such as an input tool of scissors similar to end effector scissors, or a tool that is different in shape and style to the end effector, such as an input tool of a glove dissimilar to end effector graspers, and such as an input tool of a joystick dissimilar to end effector graspers. In some embodiments, the input tool can be a larger scaled version of the end effector to facilitate ease of use. Such a larger scale input tool can have finger loops or grips of a size suitable for a user to hold. However, the end effector and the input tool can have any relative size.

A slave tool, e.g., a surgical instrument, of the surgical system can be positioned inside a patient's body cavity through an access point in a tissue surface for minimally invasive surgical procedures. Typically, cannulas such as trocars are used to provide a pathway through a tissue surface and/or to prevent a surgical instrument or guide tube from rubbing on patient tissue. Cannulas can be used for both incisions and natural orifices. Some surgical procedures require insufflation, and the cannula can include one or more seals to prevent excess insufflation gas leakage past the instrument or guide tube. In some embodiments, the cannula can have a housing coupled thereto with two or more sealed ports for receiving various types of instruments besides the slave assembly. As will be appreciated by a person skilled in the art, any of the surgical system components disclosed herein can have a functional seal disposed thereon, therein, and/or therearound to prevent and/or reduce insufflation leakage while any portion of the surgical system is disposed through a surgical access port, such as a cannula. The surgical systems can also be used in open surgical procedures. As used herein, a surgical access point is a point at which the slave tool enters a body cavity through a tissue surface, whether through a cannula in a minimally invasive procedure or through an incision in an open procedure.

The systems, devices, and methods disclosed herein can be implemented using one or more computer systems, which may also be referred to herein as digital data processing systems and programmable systems.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, e.g., a mouse, a trackball, etc., by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 15:
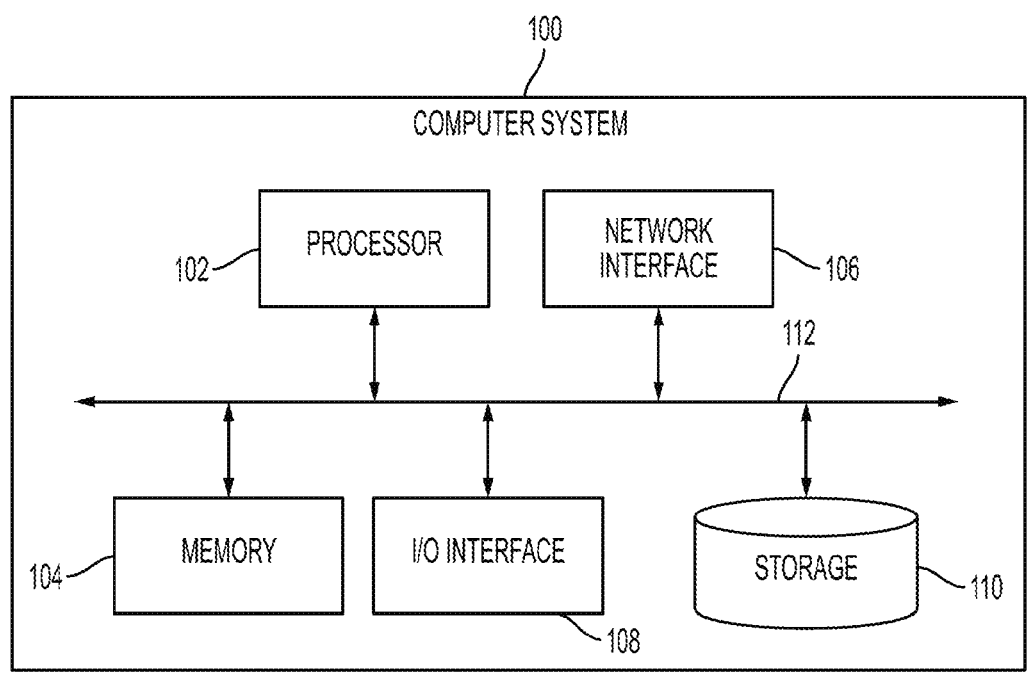
FIG. 15 illustrates an exemplary embodiment of a computer system.

FIG. 15 illustrates one exemplary embodiment of a computer system 100. As shown, the computer system 100 includes one or more processors 102 which can control the operation of the computer system 100. "Processors" are also referred to herein as "controllers." The processor(s) 102 can include any type of microprocessor or central processing unit (CPU), including programmable general-purpose or special-purpose microprocessors and/or any one of a variety of proprietary or commercially available single or multi-processor systems. The computer system 100 can also include one or more memories 104, which can provide temporary storage for code to be executed by the processor(s) 102 or for data acquired from one or more users, storage devices, and/or databases. The memory 104 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 100 can be coupled to a bus system 112. The illustrated bus system 112 is an abstraction that represents any one or more separate physical busses, communication lines/interfaces, and/or multi-drop or point-to-point connections, connected by appropriate bridges, adapters, and/or controllers. The computer system 100 can also include one or more network interface(s) 106, one or more input/output (IO) interface(s) 108, and one or more storage device(s) 110.

The network interface(s) 106 can enable the computer system 100 to communicate with remote devices, e.g., other computer systems, over a network, and can be, for non-limiting example, remote desktop connection interfaces, Ethernet adapters, and/or other local area network (IAN) adapters. The IO interface(s) 108 can include one or more interface components to connect the computer system 100 with other electronic equipment. For non-limiting example, the IO interface(s) 108 can include high speed data ports, such as universal serial bus (USB) ports, 1394 ports, Wi-Fi, Bluetooth, etc. Additionally, the computer system 100 can be accessible to a human user, and thus the IO interface(s) 108 can include displays, speakers, keyboards, pointing devices, and/or various other video, audio, or alphanumeric interfaces. The storage device(s) 110 can include any conventional medium for storing data in a non-volatile and/or non-transient manner. The storage device(s) 110 can thus hold data and/or instructions in a persistent state, i.e., the value(s) are retained despite interruption of power to the computer system 100. The storage device(s) 110 can include one or more hard disk drives, flash drives, USB drives, optical drives, various media cards, diskettes, compact discs, and/or any combination thereof and can be directly connected to the computer system 100 or remotely connected thereto, such as over a network. In an exemplary embodiment, the storage device(s) can include a tangible or non-transitory computer readable medium configured to store data, e.g., a hard disk drive, a flash drive, a USB drive, an optical drive, a media card, a diskette, a compact disc, etc.

The elements illustrated in FIG. 15 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 100 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 100 can also include a web server for generating and/or delivering the web pages to client computer systems.

In an exemplary embodiment, the computer system 100 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. No. 8,114,345 entitled "System And Method Of Sterilizing An Implantable Medical Device." It is preferred that the device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A robotic surgical system comprising:
   a robotic arm having a proximal end configured to be coupled to a support and having a driver at a distal end of the robotic arm, the driver including one or more motors;
   a tool assembly comprising
      a housing configured to releasably couple to the driver, the housing including a first actuator and a second actuator that are each actuated by at least one of the one or more motors;
      a shaft extending distally from the housing and operatively coupled to the first actuator such that actuation of the first actuator causes the shaft to rotate; and
      an end effector pivotally coupled to a distal end of the shaft, the end effector being configured to pivot upon actuation of the second actuator to form an angle between a first longitudinal axis of the end effector and a second longitudinal axis of the shaft; and
   a control system configured to control, based on the angle formed from a current position of the end effector, a velocity of movement of the robotic arm, the velocity of movement being related to the angle.

2. The robotic surgical system of claim 1, wherein the control system further controls the velocity of movement of the robotic arm based on a rotational velocity of the shaft, wherein the velocity of movement is related to the rotational velocity of the shaft.

3. A robotic surgical system comprising:
   a robotic arm having a proximal end configured to be coupled to a support and having a driver at a distal end of the robotic arm, the robotic arm being movable relative to the support;
   a tool assembly comprising
      a housing configured to releasably couple to the driver, the housing including an actuator that is actuated by a motor associated with the driver,
      a shaft extending from the housing; and
      an end effector pivotally coupled to a distal end of the shaft and configured to pivot in response to the actuator thereby defining at least one window area, each of the at least one window area having a radius that is equal to a distance between a distal end of the end effector and a longitudinal axis of the shaft; and
   a control system configured to control, based on the radius of a current position of the end effector, a velocity of movement of the robotic arm, the velocity of movement being related to the radius.

4. The robotic surgical system of claim 3, wherein the control system further controls the velocity of movement of the robotic arm based on a moment of inertia of the end effector, wherein the velocity of movement is related to the moment of inertia of the end effector.

5. The robotic surgical system of claim 3, wherein the moment of inertia is defined by one or more of a mass of the end effector, a speed of rotation of the end effector, and the distance between the distal end of the end effector and the longitudinal axis of the shaft.

6. A method comprising:
   determining a first articulation angle of an end effector located at a distal end of a shaft of a tool assembly, the tool assembly being coupled to a robotic arm of a robotic surgical system;
   setting, based on the determined first articulation angle, a first maximum velocity of movement of the robotic arm;

articulating the end effector, determining a second articulation angle of the end effector, the second articulation angle being larger than the first articulation angle; and setting, based on the determined second articulation angle, a second maximum velocity of movement of the robotic arm, the second maximum velocity of movement being less than the first maximum velocity of movement.

7. The robotic surgical system of claim 6, wherein the first and second articulation angles are each defined by an angle formed between the end effector and a longitudinal axis of the shaft.

8. The method of claim 6, further comprising rotating the end effector about a longitudinal axis of the shaft; and setting, based on the rotating of the end effector, a third maximum velocity of movement of the robotic arm, the third maximum velocity of movement being less than the second maximum velocity of movement.

9. A method comprising:

determining a first window area defined by a distal end of an end effector rotated about a longitudinal axis of a shaft of a tool assembly, the tool assembly being coupled to a robotic arm of a robotic surgical system;

setting, based on the determined first window area, a first maximum velocity of movement of the robotic arm;

articulating the end effector, determining a second window area defined by the distal end of the end effector rotated about the longitudinal axis of the shaft, the second window area being larger than the first window area; and setting, based on the determined second window area, a second maximum velocity of movement of the robotic arm, the second maximum velocity of movement being less than the first maximum velocity of movement.

10. A method comprising:

determining a first moment of inertia of an end effector located at a distal end of a shaft of a tool assembly, the tool assembly being coupled to a robotic arm of a robotic surgical system;

setting, based on the determined first moment of inertia, a first maximum velocity of movement of the robotic arm;

increasing at least one of a rotational speed of the end effector and an articulation angle of the end effector, determining a second moment of inertia of the end effector, the second moment of inertia being larger than the first moment of inertia; and setting, based on the determined second moment of inertia, a second maximum velocity of movement of the robotic arm, the second maximum velocity of movement being less than the first maximum velocity of movement.

11. The method of claim 10, wherein the moment of inertia is defined by one or more of a mass of the end effector, a speed of rotation of the end effector, and an articulation angle of the end effector.

* * * * *